US005437273A

United States Patent [19]
Bates et al.

[11] Patent Number: 5,437,273
[45] Date of Patent: Aug. 1, 1995

[54] SLIDABLE ENDOTRACHEAL TUBE HOLDER

[75] Inventors: David A. Bates, Libertyville; Barbara T. Skiba, Chicago, both of Ill.

[73] Assignee: Sage Products, Inc., Crystal Lake, Ill.

[21] Appl. No.: 88,822

[22] Filed: Jul. 8, 1993

[51] Int. Cl.⁶ .......................................... A61M 16/04
[52] U.S. Cl. ............................... 128/207.17; 128/911; 128/912; 128/DIG. 26; 128/207.14
[58] Field of Search ..................... 128/207.17, 207.18, 128/207.14, 207.15, 207.18, 200.26, 911, 912, DIG. 26

[56] References Cited

U.S. PATENT DOCUMENTS 3,946,742 3/1976 Eross ............................... 128/207.17
4,744,358 5/1988 McGinnis ...................... 128/207.17
4,906,234 3/1990 Voychehovski ............... 128/207.17
5,295,480 3/1994 Zemo ............................ 128/207.17
5,345,931 9/1994 Battaglia, Jr. ................. 128/207.17

Primary Examiner—Edgar S. Burr
Assistant Examiner—William J. Deane, Jr.
Attorney, Agent, or Firm—Lee, Mann, Smith, McWilliams, Sweeney & Ohlson

[57] ABSTRACT

A device for holding an endotracheal tube in various positions in alignment with the mouth of a patient. The tube holder has a tube holding support engaged on a frame for the holder in alignment with the mouth of a patient. The support is adjustable along the frame to position the support in various locations along the frame while still in alignment with the patient's mouth. The frame is shaped to engage the chin of a patient, and is pliant in order to conform to the chin.

17 Claims, 2 Drawing Sheets

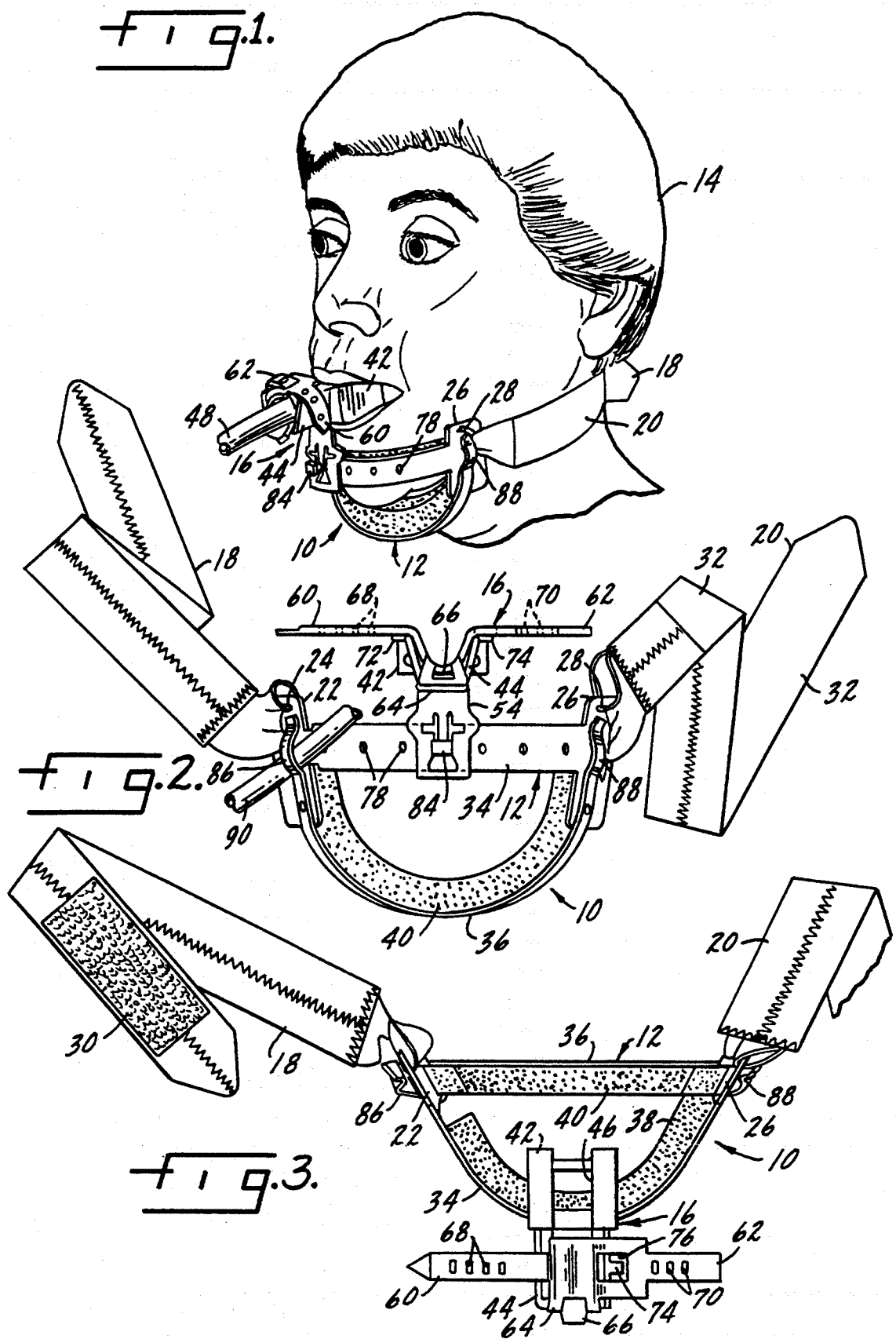

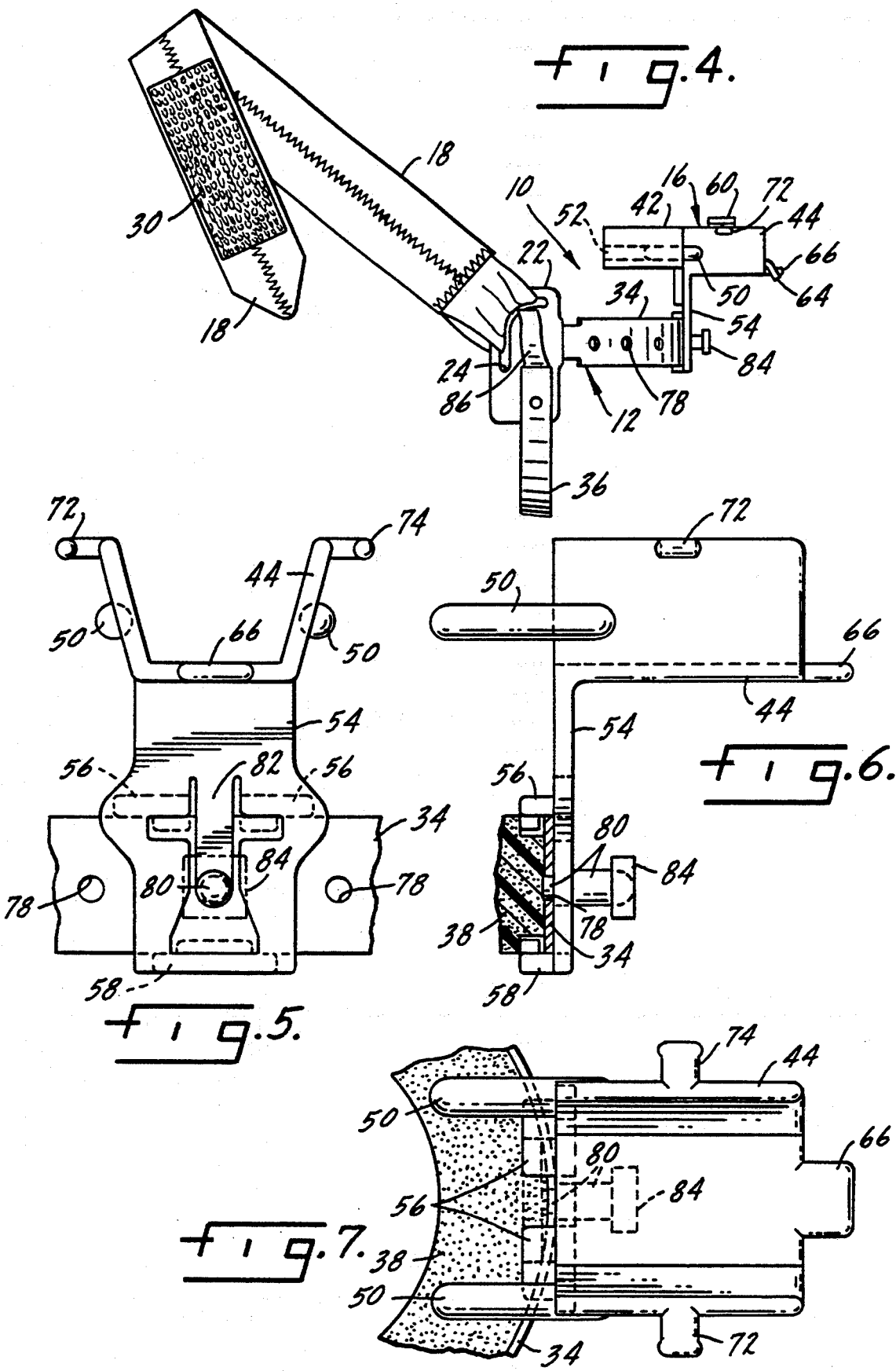

SLIDABLE ENDOTRACHEAL TUBE HOLDER

BACKGROUND OF THE INVENTION

This invention relates to devices for holding endotracheal tubes, and in particular to a device which has a tube-holding support which is positionable in various positions in order to allow access to the patient's mouth.

U.S. Pat. No. 4,744,358 discloses an endotracheal tube holder having an endotracheal tube platform held rigidly in place between two portions of a face plate frame. The rigid structure of the frame and the tube platform permits the platform to be located only in one position in the patient's mouth. Furthermore, the frame, which extends above and below the patient's mouth, substantially prevents access to the mouth. Thus, while the device of U.S. Pat. No. 4,744,358 is a significant advance over the prior art, it, in turn, suffers deficiencies which limit its usefulness.

SUMMARY OF THE INVENTION

The present invention pertains to a device for holding an endotracheal tube in alignment with the mouth of patient. It includes a frame means shaped to engage the chin of a patient, a tube-holding support engaged on the frame means in a position in alignment with the mouth of the patient, means for securing the frame means to the head of a patient, and adjustment means for changing the position of the tube holding support on the frame means.

In accordance with the preferred form of the invention, the frame means comprises a pair of frame members, one of the frame members being positioned to extend across the chin, and the other of the frame members being positioned to extend beneath the chin. The frame members are pliant in order to permit the tube holding device to conform to the chin of the patient.

The tube holding support includes a bite block having a channel for passage of an endotracheal tube. The tube holding support includes means for clamping an endotracheal tube to the bite block. The clamping means comprises a pair of flexible bands, each band including a series of apertures, and a pair of tabs situated on the support and shaped to be engaged by the apertures of the bands when drawn across an endotracheal tube. In accordance with the disclosed form of the invention, one of the bands extends through a hole in the second band.

The adjustment means comprises a slide formed in the tube-holding support which engages the frame member extending across the chin. The slide includes opposite guides extending from the support and engaging the frame member to retain the support on the frame member. The frame member thus constitutes a track upon which the slide travels.

The adjustment means includes means for locking the support to the frame member. The locking means preferably comprises a series of spaced detents in the frame member and a catch in the tube-holding support which is shaped to engage the detents. The catch comprises a pin biased toward the detents and a knob on the pin for withdrawing the pin from engagement in a detent. The pin is biased by and secured to a flexible arm formed in the tube-holding support.

BRIEF DESCRIPTION OF THE DRAWINGS

The invention is described in greater detail in the following description of an example embodying the best mode of the invention, taken in conjunction with the drawing figures, in which:

FIG. 1 is a perspective view of an endotracheal tube holder according to the invention when worn by a patient, FIG. 2 is an enlarged front elevational view of an endotracheal tube holder according to the invention, without an endotracheal tube being engaged therein, but showing a nasal tube secured in a nasal tube holder, FIG. 3 is a top plan view of the endotracheal tube holder according to FIG. 2, but with the nasal tube being removed, FIG. 4 is a side elevational view of the endotracheal tube holder according to the invention, taken from the left in FIG. 2, and again with the nasal tube removed, FIG. 5 is an enlarged front elevational view of the slidable tube-holding support, with the bite block and tube clamp being eliminated, FIG. 6 is a left side elevational illustration of the tube-holding support shown in FIG. 5, and FIG. 7 is a top plan view of the tube-holding support shown in FIG. 5.

DESCRIPTION OF AN EXAMPLE EMBODYING THE BEST MODE OF THE INVENTION

An endotracheal tube holder (hereinafter "ET holder") is shown generally at 10 in the drawing figures. The ET holder comprises three basic parts, a frame 12 which fits about the chin of a patient 14 when worn, a tube-holding support 16 and a pair of straps 18 and 20 for securing the frame 12 to the head of the patient 14.

The strap 18 is secured to the frame 12 at an ear 22 having an aperture 24 for through passage of the strap 18. Similarly, the strap 20 is secured to the frame 12 at an ear 26 having an aperture 28 therein for through passage of the strap 20. The straps 18 and 20 are of sufficient length to pass behind the head of a patient 14, as shown in FIG. 1. Preferably, the straps attach to one another with a hook-and-loop fastener (such as a Velcro brand fastener), with a hook portion 30 secured to the strap 18, and a loop portion 32 secured to the strap 20. As is conventional, a long section of the loop portion 32 is secured to the strap 20 so that the relatively shorter hook portion 30 of the strap 18 may be attached at any location along the length of the loop portion 32 depending on the size of the patient 14.

The frame 12 comprises a pair of frame members 34 and 36 extending between the ears 22 and 26. Either or both of the frame members 34 and 36 may be either secured to the ears 22 and 26, or be integral portions extending from the ears 22 and 26. It is preferred that the frame members 34 and 36 be formed of aluminum, or some other soft material that is pliant and can therefore be shaped to better fit the face of the patient 14 when the ET holder 10 is worn.

The frame member 34 is curved to extend across the chin of the patient 14. Similarly, the frame member 36 is curved to extend beneath the chin of the patient 14. Each of the frame members 34 and 36 is padded, the frame member 34 at 38, and the frame member 36 at 40, to enhance comfort of the ET holder 10 when worn. The padding 38 and 40 may be foam adhesively secured to the respective frame members 34 and 36, or any other soft material that will readily bend when the pliant frame members 34 and 36 are bent.

The tube-holding support 16 is mounted on the frame member 34. The support 16 may be formed of a single part, or two or more parts that are appropriately secured to one another. The support 16 includes a bite bar 42 extending from a clamp holder 44. The bite bar 42 has a central channel 46 which allows through passage of an endotracheal tube 48 so that when the ET holder 10 is worn by the patient 14 and the patient bites the bite bar 42, the tube 48 is not bitten by the patient, but rather is protected by the bite bar 42.

The bite bar 42 is mounted on the clamp holder 44 by means of a pair of prongs 50 extending from the clamp holder 44 and engaged in respective apertures 52 in the bite bar 42. An adhesive or other appropriate means of attachment can be used to assure the integrity of connection of the bite bar 42 to the clamp holder 44.

The clamp holder 44 has a downwardly depending body portion 54. A slide is formed in the body portion 54 for securing the tube-holding support 16 to the upper frame member 34. The slide is defined by opposite guides 56 and 58 extending from the body portion 54 over and behind the frame member 34. As best shown in FIG. 6, the frame member 34 is captured top and bottom between the guides 56 and 58, and side to side between the guides 56, 58 and the body portion 54.

As shown in FIG. 1, the endotracheal tube 48 is clamped in place in the ET holder 10 by means of a pair of flexible bands 60 and 62. The bands 60 and 62 are actually extending legs of an integral band, the band being secured within the clamp holder 44. While all means of such securing is not shown, a forward extension 64 of the flexible bands 60 and 62 extends over a tab 66 of the clamp holder 44, and the remainder of the band located within the clamp holder 44 may be adhesively secured, stapled, or otherwise attached to the clamp holder 44.

The band 60 has a series of apertures 68 therein. Similarly, the band 62 has a series of apertures 70 therein. Tabs 72 and 74 are formed on the clamp holder 44 for engaging the respective apertures 68 and 70. Also, since the bands 60 and 62 are aligned with one another, one of the bands 60 or 62 includes a hole 76 for through passage of the other band. Thus, as shown in FIG. 1, when clamped about the endotracheal tube 48, one of the bands extends through the hole 76 in the other band, with the two bands then being attached to their respective tabs 72 and 74 by the respective apertures 68 and 70. The endotracheal tube 48 is therefore clamped firmly in place.

The guides 56 and 58 permit the tube-holding support 16 to be displaced along the upper frame member 34. Thus, the positioning of the bite bar 42 and endotracheal tube 48 in the mouth of a patient 14 can be adjusted as desired, either being positioned in the center of the mouth as shown in the drawing figures, or to either side. To lock the support 16 in place at a desired location along the frame member 34, the frame member 34 is provided with a series of spaced holes or detents 78. A corresponding catch is formed in the body portion 54, the catch comprising a pin 80 shaped to engage the detents 78. The pin 80 is biased into engagement with the detents 78 by, and secured to, a flexible arm 82 formed in the body portion 54. The pin 80 also extends on the opposite side of the arm 82, terminating at a knob 84 which is used for withdrawing the pin 80 from engagement with a detent 78. The knob 84 can be formed as an integral enlargement on the end of the pin 80, or can be a separate part secured to the pin 80. Also, the pin 80, arm 82, body portion 54, prong 50 and clamp holder 44 are preferably all molded from plastic as a single part.

Due to the curvature of the frame member 34, the bite bar 42, with clamped endotracheal tube 48 therein, is always aimed into the mouth of the patient 14, no matter where the tube-holding support 16 might be positioned along the frame member 34. Thus, the attending physician or nurse can position the support 16 as desired along the frame member 34, locking the support 16 in place by engaging the pin 80 into one of the detents 78.

While the ET holder 10 is used primarily for proper positioning of an endotracheal tube 48, opposite ends of the frame member 36 are formed as clips 86 and 88 for securing a nasal-gastric tube 90 to the frame 12. A clip 86 or 88 is provided at either end of the frame member 36 so that the nasal tube 90 may be retained at either side of the face of the patient 14. Typically, the clip 86 or 88 closest to the location of the tube-holding support 16 will be that employed for the tube 90, so that access to the patient's mouth is uninhibited. Should the support 16 be located centrally on the frame member 34, either clip 86 or 88 can be employed for the tube 90.

The straps 18 and 20 may be used singly or in combination with other straps (not illustrated) to clamp the ET holder to a patient's head. Other than possibly being some part of a required means of holding the ET holder to a head, the straps 18 and 20 form no significant part of the invention.

ACHIEVEMENTS

The ET holder 10 is a significant improvement over prior endotracheal tube holders. Since the frame 12 is located fully beneath the mouth of the patient 14, access to the patient's mouth is greatly enhanced. Also, since the frame members 34 and 36 are formed of aluminum or any other flexible, bendable material, the frame 12 can be shaped appropriately to fit the chin of the patient 14, thus enhancing the comfort and stability of the ET holder 10.

Since the tube-holding support 16 is moveable laterally along the frame member 34, the endotracheal tube 48 can be positioned to enter the mouth of the patient 14 at any desired location. The support 16 is easily adjusted by simply withdrawing the pin 80 from a detent 78, and sliding the support 16 one way or the other along the frame member 34.

Various changes can be made to the invention without departing from the spirit thereof, or scope of the following claims.

What is claimed is:

1. A device for holding an endotracheal tube in alignment with the mouth of a patient, comprising
   a. frame means shaped to engage the chin of a patient,
   b. a tube-holding support engaged on said frame means in a position in alignment with the mouth of a patient,
   c. means for securing said frame means to the head of a patient, and
   d. adjustment means for changing the position of said tube-holding support on said frame means, said frame means including a frame member as a portion of said frame means, and said adjustment means including a slide formed in said tube-holding support and slidingly engaged on said frame member, said slide including opposite guides extending from said support and engaging said frame member to retain said support on said frame member, and including means for locking said support to said frame member.

2. A device according to claim 1 in which said frame means comprises a pair of frame members, one of said frame members being positioned to extend across the chin and the other of said frame members being positioned to extend beneath the chin.

3. A device according to claim 2 in which said frame members are pliant.

4. A device according to claim 1 in which said frame means is pliant.

5. A device according to claim 1 in which said tube-holding support includes a bite block having a channel for passage of an endotracheal tube.

6. A device according to claim 5 in which said tube-holding support includes means for clamping an endotracheal tube.

7. A device according to claim 6 in which said clamping means comprises a pair of flexible bands, each band including a series of apertures, and a pair of tabs on said support shaped to be engaged by the apertures of said bands.

8. A device according to claim 1 in which said tube-holding support includes means for clamping an endotracheal tube.

9. A device according to claim 8 in which said clamping means comprises a flexible band having a series of apertures, and a tab on said support shaped to be engaged by said apertures.

10. A device according to claim 1 in which said locking means comprises a series of spaced detents in said frame member and a catch in said support shaped to engage said detents.

11. A device according to claim 10 in which said catch comprises a pin biased toward said detents and a knob on said pin for withdrawing said pin from engagement in a detent.

12. A device according to claim 11 in which said pin is biased by and secured to a flexible arm formed in said support.

13. A device according to claim 1 including a nasal tube clip secured to said frame means.

14. A device for holding an endotracheal tube in alignment with the mouth of a patient, comprising
 a. frame means shaped to engage the chin of a patient, said frame means including a curved frame member positioned to extend across the chin,
 b. a tube-holding support engaged on said frame member in a position in alignment with the mouth of a patient,
 c. means for securing said frame means to the head of a patient, and
 d. adjustment means for laterally changing the position of said tube-holding support on said frame member, said adjustment means comprising a slide formed in said tube-holding support said slide including opposite guides extending from said support and engaging said frame member to retain said support slidingly engaged on said frame member.

15. A device according to claim 14 in which said locking means comprises a series of spaced detents in said frame member and a catch in said support shaped to engage said detents.

16. A device according to claim 14 in which said frame means comprises a pair of frame members, one of said frame members being positioned to extend across the chin and the other of said frame members being positioned to extend beneath the chin.

17. A device according to claim 14 including means for locking said support to said frame member.

* * * * *